(12) United States Patent
Li et al.

(10) Patent No.: US 10,757,970 B2
(45) Date of Patent: *Sep. 1, 2020

(54) ELECTRONIC SMOKING ARTICLE

(71) Applicant: Altria Client Services LLC, Richmond, VA (US)

(72) Inventors: San Li, Midlothian, VA (US); Georgios D. Karles, Richmond, VA (US); Richard Jupe, Richmond, VA (US); Gerd Kobal, Sandy Hook, VA (US); Munmaya K. Mishra, Manakin Sabot, VA (US)

(73) Assignee: Altria Client Services LLC, Richmond, VA (US)

( * ) Notice: Subject to any disclaimer, the term of this patent is extended or adjusted under 35 U.S.C. 154(b) by 79 days.

This patent is subject to a terminal disclaimer.

(21) Appl. No.: 16/117,165

(22) Filed: Aug. 30, 2018

(65) Prior Publication Data

US 2018/0368480 A1 Dec. 27, 2018

Related U.S. Application Data

(63) Continuation of application No. 15/398,165, filed on Jan. 4, 2017, now Pat. No. 10,085,487, which is a (Continued)

(51) Int. Cl.
*A24F 40/485* (2020.01)
*A24F 47/00* (2020.01)
(Continued)

(52) U.S. Cl.
CPC ............ *A24F 40/485* (2020.01); *A24D 3/048* (2013.01); *A24D 3/061* (2013.01); *A24F 47/008* (2013.01);
(Continued)

(58) Field of Classification Search
CPC ...... A24F 40/485; A24F 47/008; A61M 15/06
See application file for complete search history.

(56) References Cited

U.S. PATENT DOCUMENTS 1,945,207 A * 1/1934 Thomas ................. A24D 1/042
131/361
3,356,094 A 12/1967 Ellis et al.
(Continued)

FOREIGN PATENT DOCUMENTS

EP 0845220 A1 6/1998
EP 2319334 A1 5/2011
(Continued)

OTHER PUBLICATIONS

International Search Report and Written Opinion dated Oct. 30, 2014.
(Continued)

*Primary Examiner* — Anthony Calandra
(74) *Attorney, Agent, or Firm* — Harness, Dickey & Pierce, P.L.C.

(57) ABSTRACT

An electronic smoking article includes a liquid aerosol formulation, a heater operable to at least partially volatilize the liquid aerosol formulation and form an aerosol and a tubular filter segment downstream of the heater. The tubular filter segment is operable to selectively filter aerosol particles and vapors from the aerosol.

11 Claims, 5 Drawing Sheets

Related U.S. Application Data continuation of application No. 14/332,897, filed on Jul. 16, 2014, now Pat. No. 9,877,511.

(60) Provisional application No. 61/857,904, filed on Jul. 24, 2013.

(51) Int. Cl.
 *A61M 15/06* (2006.01)
 *A61M 11/00* (2006.01)
 *A61M 11/04* (2006.01)
 *A24D 3/04* (2006.01)
 *A24D 3/06* (2006.01)

(52) U.S. Cl.
 CPC ......... *A61M 11/003* (2014.02); *A61M 11/044* (2014.02); *A61M 15/06* (2013.01); *A61M 2205/3653* (2013.01); *A61M 2205/50* (2013.01); *A61M 2205/8206* (2013.01)

(56) References Cited

U.S. PATENT DOCUMENTS

| | | | | |
|---|---|---|---|---|
| 4,413,641 A | * | 11/1983 | Dwyer, Jr. | ............ A24D 3/045 131/330 |
| 4,517,996 A | * | 5/1985 | Vester | ................... A24D 3/043 131/339 |
| 8,353,426 B2 | | 1/2013 | Wold et al. | |
| 9,004,073 B2 | | 4/2015 | Tucker et al. | |
| 2004/0149298 A1 | | 8/2004 | Moffitt | |
| 2008/0216848 A1 | | 9/2008 | Li et al. | |
| 2009/0007925 A1 | | 1/2009 | Rasouli et al. | |
| 2011/0186063 A1 | | 8/2011 | Fiebelkorn | |
| 2013/0037041 A1 | | 2/2013 | Worm et al. | |
| 2014/0261486 A1 | | 9/2014 | Potter et al. | |

FOREIGN PATENT DOCUMENTS

| | | |
|---|---|---|
| EP | 2460422 A1 | 6/2012 |
| EP | 2471392 B1 | 9/2013 |
| WO | WO-2013076750 A1 | 5/2013 |
| WO | WO-2013098405 A2 | 7/2013 |
| WO | WO-2013098410 A2 | 7/2013 |

OTHER PUBLICATIONS

Notice of Allowance for U.S. Appl. No. 14/332,897 dated Apr. 20, 2017.

Pakistani Examination Report for corresponding Application No. 533/2014 dated Apr. 29, 2017.

\* cited by examiner

ELECTRONIC SMOKING ARTICLE

CROSS REFERENCE TO RELATED APPLICATION

This application is a Continuation of U.S. application Ser. No. 15/398,165, filed Jan. 4, 2017, which is a continuation of Ser. No. 14/332,897 filed Jul. 16, 2014, which claims priority under 35 U.S.C. § 119(e) to U.S. provisional Application No. 61/857,904, filed on Jul. 24, 2013, the entire contents of each of which are incorporated herein by reference thereto.

WORKING ENVIRONMENT

Many of the embodiments disclosed herein include electronic smoking articles operable to deliver liquid from a liquid supply reservoir to a heater. The heater volatilizes (aerosolizes) a liquid to form an aerosol.

SUMMARY OF SELECTED FEATURES

An electronic smoking article operable to produce an aerosol includes a liquid aerosol formulation; a heater operable to at least partially volatilize the liquid aerosol formulation and form an aerosol; and a tubular filter segment downstream of the heater, the tubular filter segment operable to selectively filter aerosol particles and vapors from the aerosol, whereby a particle size distribution of the aerosol is modified.

DETAILED DESCRIPTION

An electronic smoking article includes a liquid supply source (reservoir) containing a liquid aerosol formulation. The liquid aerosol formulation is delivered to a heater where the liquid aerosol formulation is heated, volatilized, and forms an aerosol. As used herein, the term "electronic smoking article" is inclusive of all types of electronic smoking articles, regardless of form, size or shape, including electronic cigarettes, electronic cigars, electronic pipes, electronic hookahs and the like. The liquid aerosol formulation can include nicotine or be nicotine free. Moreover, the liquid aerosol formulation can include tobacco flavors or instead, or in combination include other suitable flavors.

Preferably, the aerosol passes through a tubular filter segment after formation to selectively filter aerosol particles and vapors, elute flavor and/or otherwise modify the aerosol composition. While not wishing to be bound by theory, it is believed that the tubular filter segment selectively filters out smaller particles and vapor phase components from the aerosol as the aerosol passes through the tubular filter segment, while larger particles are maintained centrally within the aerosol flow as the aerosol passes through the tubular filter segment.

Figure 1:
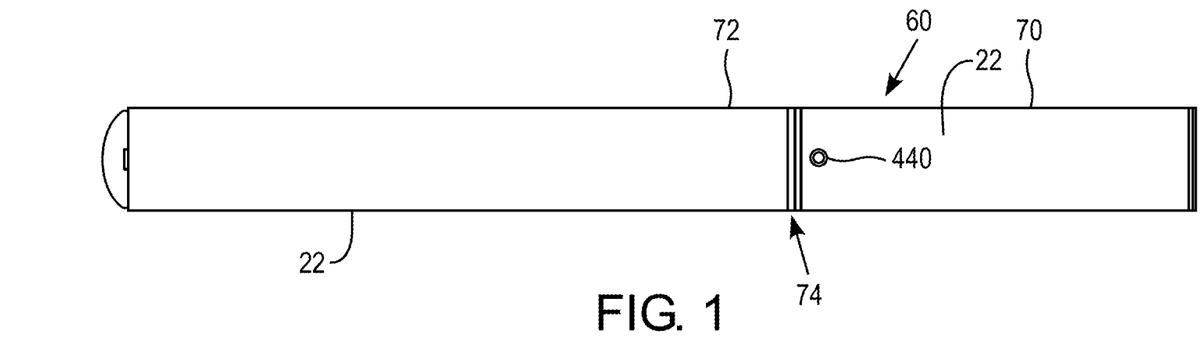
FIG. 1 is a side view of an electronic smoking article constructed according to the teachings herein.

Preferably, the tubular filter segment (TFS) 600 is located downstream of the heater in an electronic smoking article 60 as shown in FIGS. 2, 3, 4, 6, 8 and 9. As shown in FIG. 1, the electronic smoking article 60 comprises a replaceable cartridge (or first section) 70 and a reusable fixture (or second section) 72, which are coupled together at a threaded joint 74 or by other convenience such as a snug-fit, snap-fit, detent, clamp and/or clasp.

Figure 3:
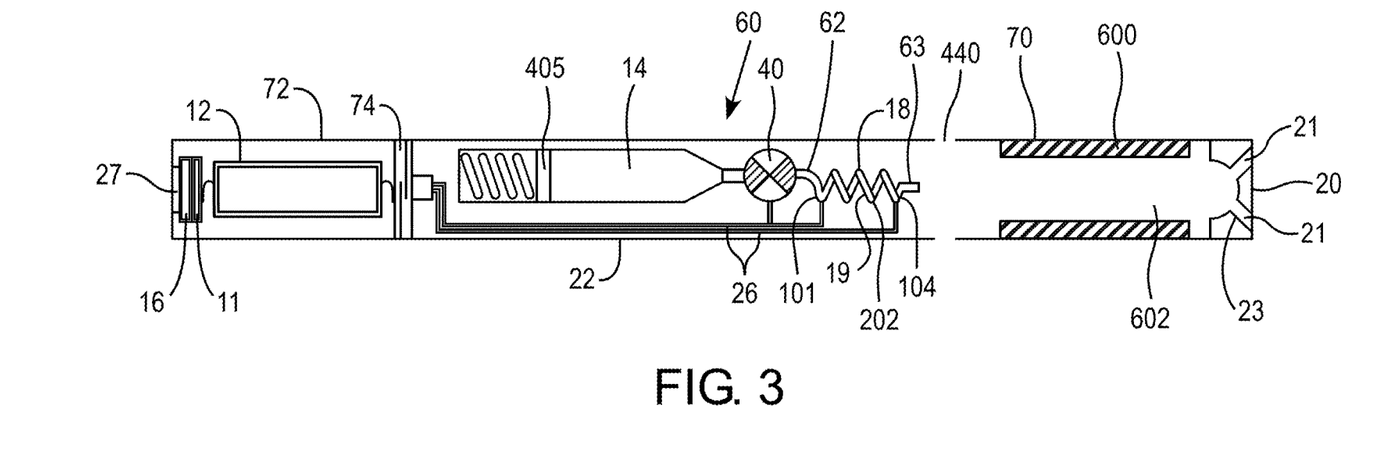
FIG. 3 is a cross-sectional view of another embodiment of an electronic smoking article according to a second embodiment.

As shown in FIG. 3, the first section 70 can house a mouth-end insert 20, a capillary aerosol generator including a capillary (capillary tube) 18, a heater 19 to heat at least a portion of the capillary 18, a reservoir 14 and optionally a valve 40. Alternatively, as shown in FIG. 4, the first section 70 can house a mouth end insert 20, a heater 319, a flexible, filamentary wick 328 and a reservoir 314 as discussed in further detail below.

Figure 4:
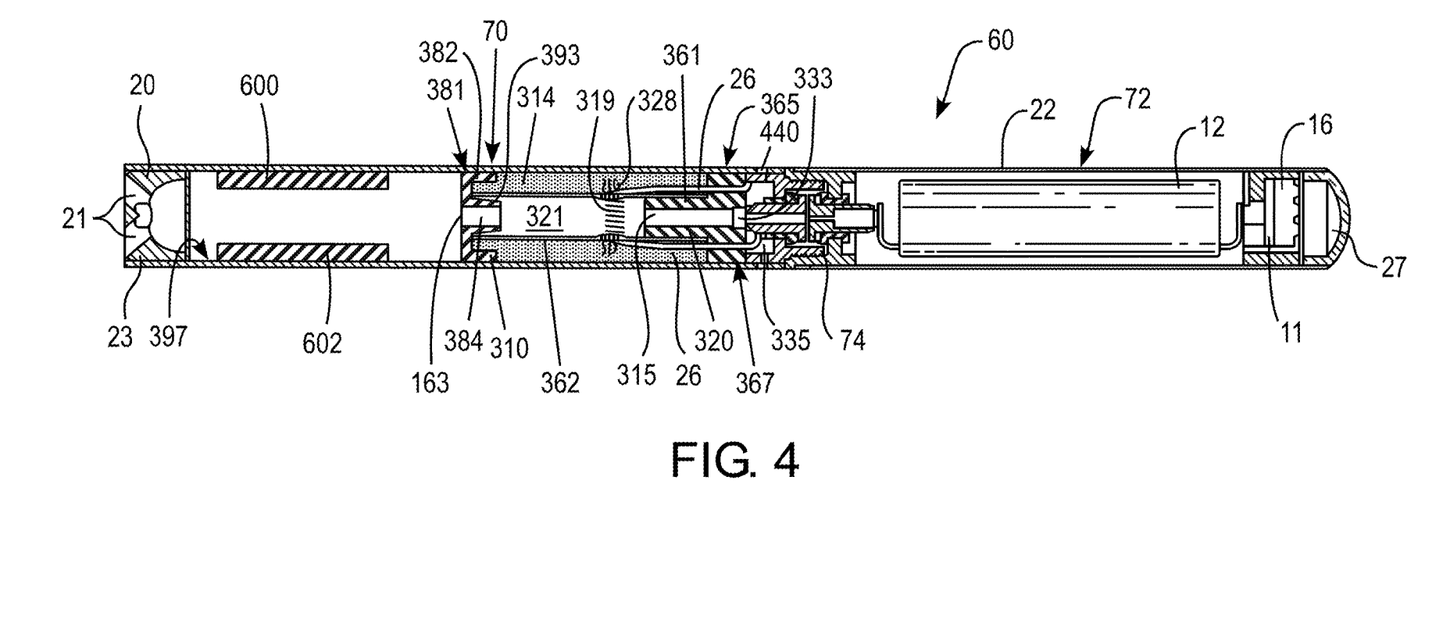
FIG. 4 is a cross-sectional view of an electronic smoking article according to a third embodiment.
Figure 5:
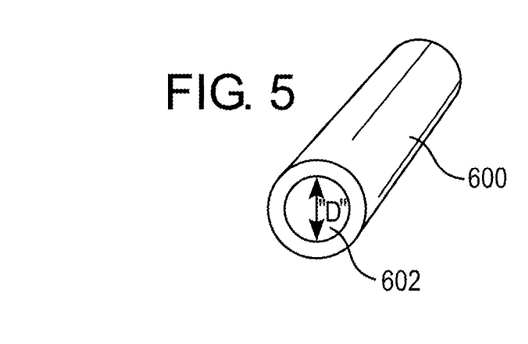
FIG. 5 is a perspective view of a tubular filter segment as described herein.

The second section 72 can house a power supply 12 (shown in FIGS. 2, 3 and 4), control circuitry 11, and optionally a puff sensor 16 (shown in FIGS. 3 and 4). The threaded portion 74 of the second section 72 can be connected to a battery charger when not connected to the first section 70 for use so as to charge the battery.

Figure 2:
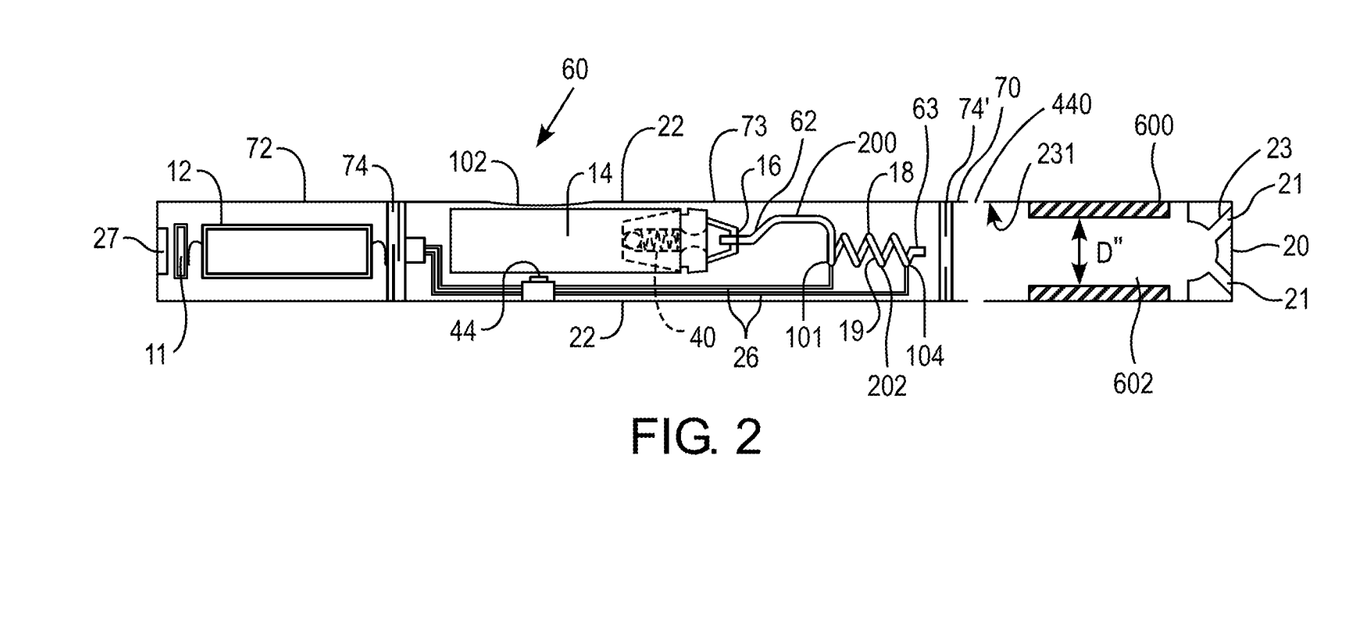
FIG. 2 is a cross-sectional view of an electronic smoking article according to a first embodiment.

As shown in FIG. 2, the electronic smoking article 60 can also include a middle section (third section) 73, which can house the reservoir 14, heater 19 and valve 40. The middle section 73 can be adapted to be fitted with a threaded joint 74' at an upstream end of the first section 70 and a threaded joint 74 at a downstream end of the second section 72. In this embodiment, the first section 70 houses the mouth-end insert 20, while the second section 72 houses the power supply 12 and control circuitry.

Preferably, the first section 70, the second section 72 and the optional third section 73 include an outer cylindrical housing 22 extending in a longitudinal direction along the length of the electronic smoking article 60. Moreover, in one embodiment, the middle section 73 is disposable and the first section 70 and/or second section 72 are reusable. In another embodiment, the first section 70 can also be replaceable so as to avoid the need for cleaning the capillary 18 and/or heater 19. The sections 70, 72, 73 can be attached by threaded connections whereby the middle section 73 can be replaced when liquid in the reservoir 14 is used up.

It is contemplated that the housing may be a single, unitary element without any threaded connections.

As shown in FIG. 2, the outer cylindrical housing 22 can include a cutout or depression 102 which allows a smoker (vaporer) to manually apply pressure to the reservoir 14. Preferably, the outer cylindrical housing 22 is flexible and/or compressible along the length thereof and fully or partially covers the reservoir 14. The cutout or depression 102 can extend partially about the circumference of the outer cylindrical housing 22. Moreover, the reservoir 14 is compressible such that when pressure is applied to the reservoir, liquid is pumped from the reservoir 14 to the capillary 18. A pressure activated switch 44 can be positioned beneath the reservoir 14. When pressure is applied to the reservoir 14 to pump liquid, the switch is also pressed and a heater 19 is activated. The heater 19 can be a portion of the capillary 18.

In the embodiment of FIG. 2, the reservoir 14 is a tubular, elongate body formed of an elastomeric material so as to be flexible and/or compressible when squeezed. Preferably, the elastomeric material can be selected from the group consisting of silicone, plastic, rubber, latex, and combinations thereof.

Preferably, the compressible reservoir 14 has an outlet 16 which is in fluid communication with a capillary 18 so that when squeezed, the reservoir 14 can deliver a volume of liquid material to the capillary 18. Simultaneous to delivering liquid to the capillary, the power supply 12 is activated upon application of manual pressure to the pressure switch and the capillary 18 is heated to form a heated section wherein the liquid material is volatilized. Upon discharge from the heated capillary 18, the volatilized material expands, mixes with air and forms an aerosol.

Preferably, the reservoir 14 extends longitudinally within the outer cylindrical housing 22 of the first section 70 (shown in FIGS. 3 and 4) or the middle section 73 (shown in FIG. 2). Moreover, the reservoir 14 comprises a liquid aerosol formulation which is volatilized when heated and forms an aerosol when discharged from the capillary 18.

In the preferred embodiments shown in FIGS. 2 and 3, the capillary 18 includes an inlet end 62 in fluid communication with the outlet 16 of the reservoir 14, and an outlet end 63 operable to expel volatilized liquid material from the capillary 18. In a preferred embodiment, as shown in FIGS. 2 and 3, the reservoir 14 may include a valve 40.

As shown in FIG. 2, the valve 40 can be a check valve that is operable to maintain the liquid material within the reservoir, but opens when the reservoir 14 is squeezed and pressure is applied. Preferably, the check valve 40 opens when a critical, minimum pressure is reached so as to avoid inadvertent dispensing of liquid material from the reservoir 14 or activating the heater 19. Once pressure upon the reservoir 14 is relieved, the valve 40 closes. The heated capillary 18 discharges liquid remaining downstream of the valve 40.

As shown in FIG. 3, in other embodiments, the valve 40 can be a two-way valve and the reservoir 14 can be pressurized. For example, the reservoir 14 can be pressurized using a pressurization arrangement 405 which applies constant pressure to the reservoir 14. For example, pressure can be applied to the reservoir 14 using an internal or external spring and plate arrangement which constantly applies pressure to the reservoir 14. Alternatively, the reservoir 14 can be compressible and positioned between two plates that are connected by springs or the reservoir 14 could be compressible and positioned between the outer housing and a plate that are connected by a spring so that the plate applies pressure to the reservoir 14.

Preferably, the capillary 18 of FIGS. 2 and 3 has an internal diameter of 0.01 to 10 mm, preferably 0.05 to 1 mm, and more preferably 0.05 to 0.4 mm. Also preferably, the capillary 18 may have a length of about 5 mm to about 72 mm, more preferably about 10 mm to about 60 mm or about 20 mm to about 50 mm. In one embodiment, the capillary 18 is substantially straight. In other embodiments, the capillary 18 is coiled and/or includes one or more bends therein to conserve space and/or accommodate a long capillary.

In these embodiments, the capillary 18 is formed of a conductive material, and thus acts as its own heater 19 by passing current through the capillary. The capillary 18 may be any electrically conductive material capable of being resistively heated, while retaining the necessary structural integrity at the operating temperatures experienced by the capillary 18, and which is non-reactive with the liquid material. Suitable materials for forming the capillary 18 are selected from the group consisting of stainless steel, copper, copper alloys, porous ceramic materials coated with film resistive material, Inconel® available from Special Metals Corporation, which is a nickel-chromium alloy, nichrome, which is also a nickel-chromium alloy, and combinations thereof.

Alternatively, the capillary 18 may be a non-metallic tube such as, for example, a glass tube having a conductive material capable of being resistively heated, such as, for example, stainless steel, nichrome or platinum wire, arranged there along.

Preferably, at least two electrical leads 26 are bonded to a metallic capillary 18 by brazing or crimping. Preferably, one electrical lead 26 is attached to a first, upstream portion 101 of the capillary 18 and a second electrical lead 26 is attached to a downstream, end portion 104 of the capillary 18, as shown in FIGS. 2 and 3.

As noted above, the liquid aerosol formulation can also be used in an electronic smoking article including a heater 319 and a filamentary wick 328 as shown in FIG. 4. The first section 70 includes an outer tube (or casing) 22 extending in a longitudinal direction and an inner tube (or chimney) 362 coaxially positioned within the outer tube 322. Preferably, a nose portion 361 of an upstream gasket (or seal) 320 is fitted into an upstream end portion 365 of the inner tube 362, while at the same time, an outer perimeter 367 of the gasket 320 provides a liquid-tight seal with an interior surface 397 of the outer casing 22. The upstream gasket 320 also includes a central, longitudinal air passage 315, which opens into an interior of the inner tube 362 that defines a central channel 321. A transverse channel 333 at an upstream portion of the gasket 320 intersects and communicates with the central channel 315 of the gasket 320. This channel 333 assures communication between the central channel 315 and a space 335 defined between the gasket 320 and a threaded connection 74.

Preferably, a nose portion 393 of a downstream gasket 310 is fitted into a downstream end portion 381 of the inner tube 362. An outer perimeter 382 of the gasket 310 provides a substantially liquid-tight seal with an interior surface 397 of the outer casing 22. The downstream gasket 310 includes a central channel 384 disposed between the central passage 321 of the inner tube 362 and the mouth end insert 20.

In this embodiment, the reservoir 314 is contained in an annulus between an inner tube 362 and an outer casing 22 and between the upstream gasket 320 and the downstream gasket 310. Thus, the reservoir 314 at least partially surrounds the central air passage 321. The reservoir 314 comprises a liquid material and optionally a liquid storage medium (not shown) operable to store the liquid material therein.

The inner tube 362 has a central air passage 321 extending therethrough which houses the heater 319. The heater 319 is in contact with the filamentary wick 328, which preferably extends between opposing sections of the reservoir 314 so as to deliver the liquid aerosol formulation from the reservoir to the heater 319.

Preferably, the electronic smoking article 60 of each embodiment described herein also includes at least one air inlet 440. As shown in FIG. 4, the at least one air inlet 440 can be located upstream of the heater 319.

In the embodiments shown in FIGS. 2 and 3, the at least one air inlet 440 is arranged downstream of the capillary 18 so as to minimize drawing air along the capillary and thereby avoid cooling of the capillary 18 during heating cycles.

The power supply 12 of each embodiment can include a battery arranged in the electronic smoking article 60. The power supply 12 is operable to apply voltage across the heater 19 associated with the capillary 18, as shown in FIGS. 2 and 3, or the heater 319 associated with the filamentary wick 328, as shown in FIG. 4. Thus, the heater 19, 319 volatilizes liquid material according to a power cycle of either a predetermined time period, such as a 2 to 10 second period.

The battery can be a Lithium-ion battery or one of its variants, for example a Lithium-ion polymer battery. Alternatively, the battery may be a Nickel-metal hydride battery, a Nickel cadmium battery, a Lithium-manganese battery, a Lithium-cobalt battery or a fuel cell. In that case, preferably, the electronic smoking article 60 is usable by a smoker until the energy in the power supply is depleted. Alternatively, the power supply 12 may be rechargeable and include circuitry allowing the battery to be chargeable by an external charging device. The control circuitry 11 can be programmable and can include an application specific integrated circuit (ASIC). In other embodiments, the control circuitry 11 can include a microprocessor programmed to carry out functions such as heating the capillaries and/or operating the valves.

Preferably, the electronic smoking article 60 of each embodiment also includes control circuitry which can be on a printed circuit board 11 (shown in FIGS. 2, 3 and 4). The control circuitry 11 can also include a heater activation light 27 that is operable to glow when the heater 19, 319 is activated.

As shown in FIGS. 2, 3, 4, 6, 8 and 9 the electronic smoking article 60 includes the tubular filter segment 600 at a location downstream of the heater 19, 319. Preferably, the tubular filter segment 600 is constructed from low density cellulose acetate tow and is a hollow acetate tube (HAT). The tubular filter segment 600 can be about 2 mm to about 30 mm in length. More preferably, the tubular filter segment 600 is about 5 mm to about 25 mm in length (e.g., about 10 to about 20 mm or about 12 to about 18 mm). Also preferably, the tubular filter segment 600 is about 0.5 mm to about 6 mm thick (e.g., about 2 mm to about 5 mm or about 3 mm to about 4 mm). In addition, the outer diameter of the tubular filter segment 600 is about the same or slightly greater than a diameter of the electronic smoking article 60 so as to provide an interference (snug) fit between the two.

Moreover, as shown in FIGS. 2, 3, 4, 5, 6, 7 and 8, the tubular filter segment 600 includes a hollow core 602 having a diameter "D" (shown in FIGS. 2 and 5) of about 1 mm to about 6 mm (e.g., about 2 mm to about 5 mm or about 3 mm to about 4 mm). In one embodiment, the diameter of the hollow core 602 is uniform along the length of the tubular filter segment 600. In another embodiment, the hollow core 602 can have a diameter that varies along the length of the tubular filter segment 600. Thus, the aerosol flow can have a straight, bended or twisted path. Different flow paths may contribute to a different degree of potential filtration by impaction and also cooling of the aerosol.

Aerosol filtration during smoking (vaping) can be accomplished by impaction, interception and/or diffusion. Moreover, the tubular filter segment 600 could have electrostatic filtration mechanisms, which can aid in filtering the aerosol.

The diameter of the hollow core 602 can be chosen so that only a certain size range of aerosol particles will encounter the tubular filter segment 600 and be removed from the aerosol flow. Moreover, the distance of the tubular filter segment 600 from the heater 19, 319 can be chosen based on the different trajectories of the aerosol tube to produce different interactions with the tubular filter segment 600 during smoking, and thus different sensory experiences. If the tubular filter segment 600 is closer to the heater, a smaller amount of the aerosol will be exposed to the tubular filter segment 600. However, if the tubular filter segment 600 is positioned farther away from the heater, a larger amount of the aerosol will be exposed to the tubular filter segment 600. Moreover, depending on the thickness and density of the tubular filter segment 600, different degrees of aerosol filtration may be achieved as the aerosol is passing through or around the periphery of the tubular filter segment 600.

In another embodiment, the tubular filter segment 600 can be formed of porous foam, paper or other cellulosic materials so long as the material is air transmissive. The tubular filter segment 600 can be made via other forming techniques such as molding or extruding the tube or forming a tube with a longitudinal seam.

Figure 7:
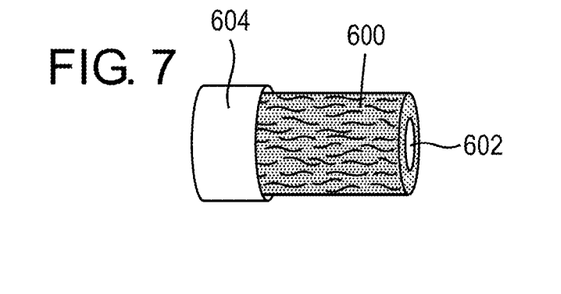
FIG. 7 is a perspective view of a detachable tubular filter segment.
Figure 8:
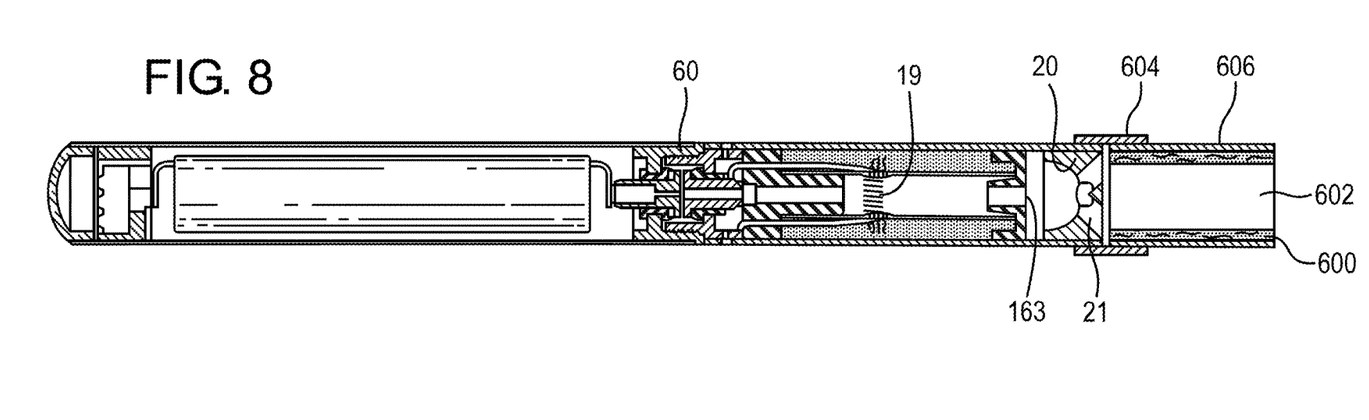
FIG. 8 is a cross-sectional view of an electronic smoking article according to a fifth embodiment including the detachable tubular filter segment of FIG. 7.

In the preferred embodiment, the tubular filter segment 600 minimizes resistance to draw (RTD) in the electronic smoking article 60 and can be included inside the first section 70 during manufacture or can be a detachable tubular filter segment, as shown in FIGS. 7 and 8, for addition to the electronic smoking article if desired.

As shown in FIGS. 7 and 8, the detachable tubular filter segment 600 can include a sleeve portion 604 designed to fit around the outer perimeter of the mouth end of the electronic smoking article 60.

Figure 6:
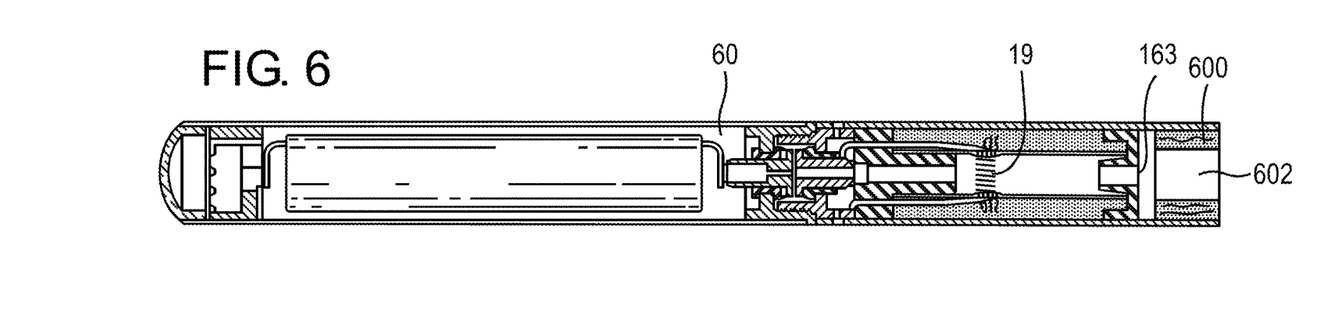
FIG. 6 is a cross-sectional view of an electronic smoking article according to a fourth embodiment including the tubular filter segment of FIG. 5.

As shown in FIG. 6, the electronic smoking article 60 can include the tubular filter segment 600 at the mouth end of the electronic smoking article 60. In other embodiments, shown in FIG. 4, a mouth end insert 20 can be positioned downstream of the tubular filter segment 600. Alternatively, the mouth end insert 20 can be positioned upstream of the tubular filter segment 600 as shown in FIG. 8.

Figure 9:
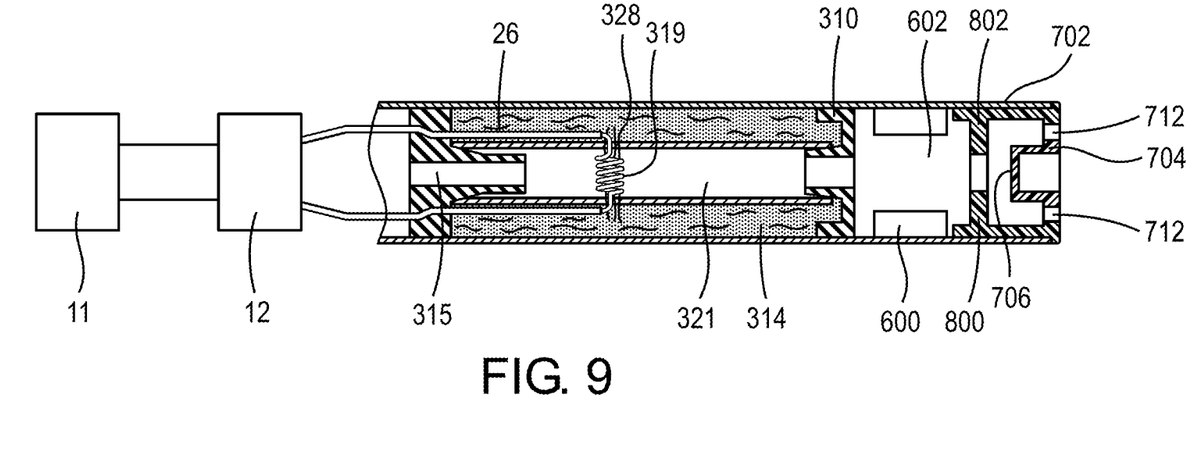
FIG. 9 is an abbreviated, cross-sectional view of an electronic smoking article according to a sixth embodiment including a tubular filter segment and a mechanical airflow convertor (MAC) insert.

In yet another embodiment, as shown in FIG. 9, the electronic smoking article 60 can include the tubular filter segment 600 and a mechanical aerosol converter (MAC) insert 704 as described in commonly owned, co-pending patent application Ser. No. 13/756,067 filed Jan. 31, 2013, the entire content of which is incorporated herein by reference thereto for all purposes. The MAC insert 704 comprises a cylindrical body portion 706 having an outer diameter that can be sized to provide a sliding fit with the interior surfaces of the outer housing 22 of the electronic smoking article 60. During smoking and after passing through the tubular filter segment 600, the aerosol is drawn into contact with a face 702 of the MAC insert 704. After contacting the face 702 of the MAC insert 704, aerosol is then drawn through the orifices 712 in the MAC insert 704, which are disposed radially about the face 702. A gasket 800 having a central orifice 802 can be positioned upstream of the MAC insert 704 so as to focus the aerosol on the face 702. Accordingly, larger particle in the aerosol will impact the face 702 and get filtered out or break up prior to the aerosol being drawn out of the electronic smoking article. It is also believed that the tubular filter section 600 assists in thermal transfer thus cooling down the aerosol and improving the sensorial attributes thereof.

In a preferred embodiment, additives including flavors and/or aerosol modifiers can be applied to the tubular filter segment 600 so that additives are eluted into the aerosol as the aerosol passes therethrough. For example, the additives can be applied as a coating on the inner surface of the hollow core 602, as a coating 606 on an outer surface of the tubular filter segment 600 (shown in FIG. 8) or the flavors and/or aerosol modifiers can be impregnated in the tubular filter segment 600. The additives can be microencapsulated with water soluble materials having varying levels of water solubility so as to provide controlled release of the additive over a period of time. Moreover, the tubular filter segment 600 can include impregnated additives and an additive coating. The coating material can include the same additive as that contained in the tubular filter segment 600 or a different additive. By including an additive-containing coating along with the additives impregnated in the tubular filter segment 600, release of the additives can be staggered during smoking and/or multiple additives can be delivered. The heat of the aerosol could also help to promote release of additives from the tubular filter segment 600.

As used herein, the term "additive" means any material which modifies the characteristics of the electronic smoking article 60 when the electronic smoking article 60 is vaped. Any appropriate additive material or combination of materials may be contained in the tubular filter segment 600. Such additive materials include flavor materials, aromatic materials, pH modifying agents (e.g., buffers and/or acids), chemesthesis agents including cooling agents and warming agents, carbon dioxide formers, commercially available flavor systems, nicotine in liquid, salt or powder form, and other aerosol modifiers.

As used herein, the term "flavor material" means any liquid or solid flavor containing material or formulation that can release flavors and/or aromas into the aerosol stream. Suitable flavors or flavorings include, but are not limited to, menthol, mint, such as peppermint and spearmint, chocolate, licorice, citrus and other fruit flavors, gamma octalactone, vanillin, ethyl vanillin, breath freshener flavors, spice flavors such as cinnamon, methyl salicylate, linalool, bergamot oil, geranium oil, lemon oil, ginger oil, and tobacco flavor. Other suitable flavors may include flavor compounds selected from the group consisting of an acid, an alcohol, an ester, an aldehyde, a ketone, a pyrazine, combinations or blends thereof and the like.

The flavor material can be in the form of particles, granules, fibers, capsules, microcapsules, powders, crushed plant material, aromatic barks, seeds, pieces of dried fruits and/or root material, or any other suitable form. For example, the flavor material can include tobacco beads, tobacco powder or tobacco particles (filler), flavor beads, mentholated flavor beads, flavor capsules and other flavor materials as used in traditional tobacco smoke filters.

Suitable flavor materials can be non-volatile or volatile and can be delivered to the mouth via the condensation of the aerosol in the filter followed by entrapment and/or dissolution of the flavor material in droplets and/or deposition of the droplets to the tongue of the smoker during a puff. Another potential mechanism can be the physical displacement of liquid or particulate additives by the air flow. The droplets can consist of constituents used to form the aerosol including propylene glycol, glycerin, water and optionally nicotine. The flavor material can be released into the aerosol and/or can be delivered to a smoker's mouth via contact with moisture from the smoker's lips.

The flavor materials can provide a bitter taste. Suitable compounds which provide a bitter taste include, without limitation, caffeine, denatonium benzoate, theobromine, quinine, and naringin.

The flavor materials can provide a sour taste. Suitable compounds which provide a sour taste include, without limitation, citric acid, malic acid, succinic acid and tartaric acid.

The flavor materials can provide a salty taste. Suitable compounds which provide a salty taste include, without limitation, sodium chloride and potassium chloride.

The flavor materials can provide a sweet taste. Suitable compounds which provide a sweet taste include, without limitation, carbohydrates, including sucrose, and high intensity sweeteners, including sucralose and saccharin.

The flavor materials can provide umami and mouth feel. Suitable compounds which provide umami and mouth feel include, without limitation, monosodium glutamate, gamma-glutamyl peptides, such as gamma-glutamycysteine-beta-alanine, (R)-strombine.

In one embodiment, the additive can be a chemesthesis agent and/or can be chosen to alter the mouthfeel of the aerosol. For example, the additive can be a chemesthesis agent that provides a warm, tingling sensation and/or a cooling sensation. Additives such as capsaicin, piperine, alpha-hydroxy-sanshool, and (8)-gingerole can be included to provide a warm, tingling or burning sensation. Additives including menthol, menthyl lactate, WS-3 (N-Ethyl-p-menthane-3-carboxamide), WS-23 (2-Isopropyl-N,2,3-trimethylbutyramide) and Evercool 180™ can be included to provide a cooling sensation. In addition, the additive can include extracts, such as coffee extract, red pepper extract, ginger extract and peppermint oil.

During smoking, as aerosol travels through the tubular filter segment 600, larger particles remain centrally located in the flow path while smaller particles and vapor phase components diffuse to the periphery of the flow path and contact the tubular filter segment. Accordingly, the smaller particles and vapor phase components can be filtered out from the aerosol. When additives are impregnated in and/or coated on the tubular filter segment, the additives can be at least partially eluted into the aerosol for delivery to the smoker.

Preferably, the tubular filter segment 600 is located downstream of the heater 19, 319 so that minimum heat exposure is experienced by the additives. Thus, preferably, the tubular filter segment 600 is located so that the tubular filter segment 600 and/or additives contained therein are not exposed to temperatures above about 150° C.

For example, the tubular filter segment can be a hollow acetate tube (HAT) having a length of about 7 mm, an outer diameter of about 7 mm and an inner diameter of about 5 mm. The HAT can be treated with a solution of 10% triacetin and 10% citric acid and placed at the exit of the inner channel 321 (shown in FIG. 4). Aerosol particles with different trajectories will interact with the HAT differently and at different physical locations. Chemical analysis of the HAT after smoking shows significant amount of nicotine, indicating filtration of at least some vapor phase nicotine and aerosol particles by the HAT. Moreover, it is believed that the vapor phase nicotine can interact with the citric acid applied to the HAT so as to reduce harshness and improve the sensory experience.

As shown in FIGS. 2, 3, 4, and 8, the electronic smoking article 60 can further include the mouth-end insert 20 having at least two off-axis, preferably diverging outlets 21. Preferably, the mouth-end insert is located downstream of the tubular filter segment 600. In other embodiments, as shown in FIG. 8, the tubular filter segment 600 can be downstream of the mouth-end insert 20.

Preferably, the mouth-end insert 20 includes at least two diverging outlets 21. (e.g. 3, 4, 5, or preferably 6 to 8 outlets or more). Preferably, the outlets 21 of the mouth-end insert 20 are located at ends of off-axis passages 23 and are angled outwardly in relation to the longitudinal direction of the electronic smoking article 60 (i.e., divergently). As used herein, the term "off-axis" denotes at an angle to the longitudinal direction of the electronic smoking article.

In a preferred embodiment, the electronic smoking article 60 is about the same size as a conventional smoking article. In some embodiments, the electronic smoking article 60 can be about 80 mm to about 110 mm long, preferably about 80 mm to about 100 mm long and about 7 mm to about 8 mm in diameter. For example, in an embodiment, the electronic smoking article is about 84 mm long and has a diameter of about 7.8 mm.

The outer cylindrical housing 22 of the electronic smoking article 60 may be formed of any suitable material or combination of materials.

Preferably, the liquid aerosol formulation for use in each of the electronic smoking articles 60 described herein includes at least one aerosol former, water, and flavors. The liquid aerosol formulation can include nicotine or be nicotine free. Moreover, the liquid aerosol formulation can include tobacco flavors or other suitable flavors.

In the preferred embodiment, the at least one aerosol former is selected from the group consisting of propylene glycol, glycerin and combinations thereof. Preferably, the at least one aerosol former is included in an amount ranging from about 40% by weight based on the weight of the liquid formulation to about 90% by weight based on the weight of the liquid formulation (e.g., about 50% to about 80%, about 55% to about 75% or about 60% to about 70%).

Preferably, the liquid formulation also includes water. Water can be included in an amount ranging from about 5% by weight based on the weight of the liquid formulation to about 20% by weight based on the weight of the liquid formulation, more preferably in an amount ranging from about 10% by weight based on the weight of the liquid formulation to about 15% by weight based on the weight of the liquid formulation.

The liquid aerosol formulation optionally includes at least one flavorant in an amount ranging from about 0.2% to about 15% by weight (e.g., about 1% to about 12%, about 2% to about 10%, or about 5% to about 8%). The at least one flavorant can be a natural flavorant or an artificial flavorant. Preferably, the at least one flavorant is selected from the group consisting of tobacco flavor, menthol, wintergreen, peppermint, herb flavors, fruit flavors, nut flavors, liquor flavors, and combinations thereof.

Figure 10:
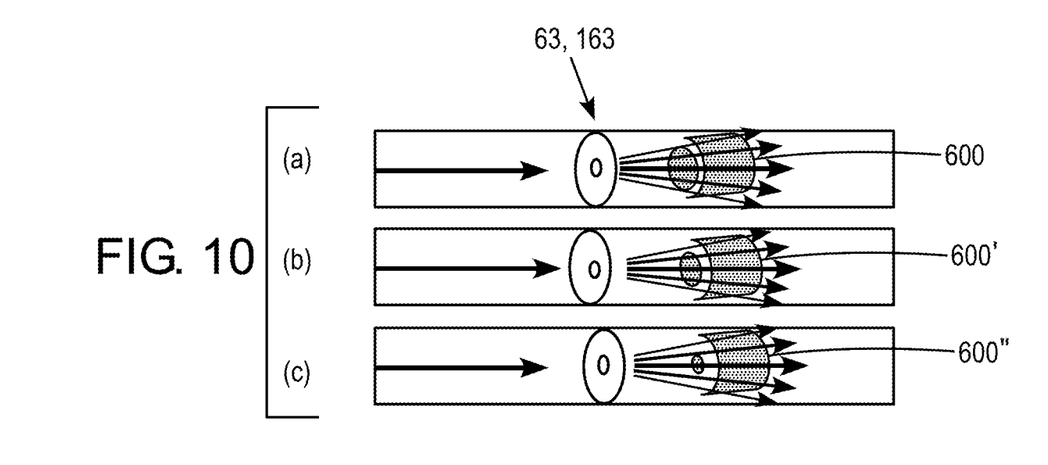
FIG. 10 is a representation of the effects achieved of using tubular filter segments of differing internal diameters.
Figure 11:
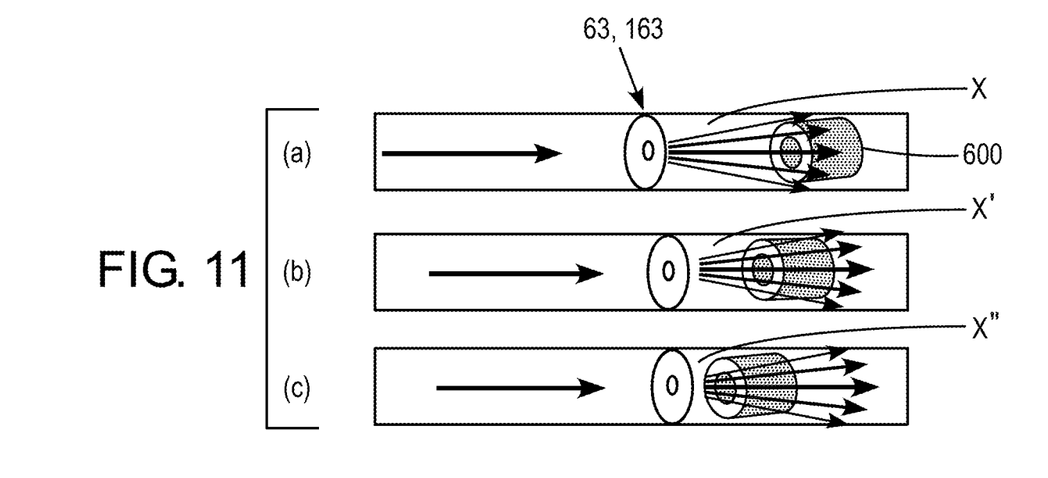
FIG. 11 is a representation of the effects of using differing spacings (x) between the tubular filter segment and the source of the aerosol.

Referring to FIGS. 10*a*, 10*b*, and 10*c*, a representation is provided wherein the source of aerosol is designated as 63, 163 which are represented as the discharge orifice 63 of the heated capillary or the discharge orifice 163 of the inner tube shown in FIGS. 6 and 8. Progressing from FIGS. 10*a* to 10*c*, as the inner diameter of the TFS 600 is reduced, a greater proportion of the aerosol passes through the body of the TFS 600, so as to reduce the population of larger particles in the aerosol that leaves the electronic smoking article 60. Particle size distribution of the aerosol can be adjusted accordingly. Likewise, now referring to FIGS. 11*a*, 11*b*, and 11*c*, as a distance x between the source of aerosol 63,163 and the TFS 600 is decreased (progressing from FIG. 11*a* to 11*c*, a smaller proportion of the aerosol passes through the body of the TFS 600 so as to lessen impact of the TFS 600 on the particle size distribution of the aerosol which ultimately leaves the electronic smoking article 60.

When the word "about" is used in this specification in connection with a numerical value, it is intended that the associated numerical value include a tolerance of ±10% around the stated numerical value. Moreover, when reference is made to percentages in this specification, it is intended that those percentages are based on weight, i.e., weight percentages.

Moreover, when the words "generally" and "substantially" are used in connection with geometric shapes, it is intended that precision of the geometric shape is not required but that latitude for the shape is within the scope of the disclosure. When used with geometric terms, the words "generally" and "substantially" are intended to encompass not only features which meet the strict definitions but also features which fairly approximate the strict definitions.

It will now be apparent that a new, improved, and nonobvious electronic smoking article has been described in this specification with sufficient particularity as to be understood by one of ordinary skill in the art. Moreover, it will be apparent to those skilled in the art that numerous modifications, variations, substitutions, and equivalents exist for features of the electronic smoking article which do not materially depart from the spirit and scope of the invention. Accordingly, it is expressly intended that all such modifications, variations, substitutions, and equivalents which fall within the spirit and scope of the invention as defined by the appended claims shall be embraced by the appended claims.

We claim:

1. A cartridge of an electronic article comprising:

a housing;

a heater in the housing, the heater configured to heat a formulation to form a vapor; and a filter formed of a hollow acetate tube including a hollow inner core, the filter having a length, the hollow inner core having an inner diameter that varies along an entirety of the length of the filter, the filter between the heater and a mouth end of the cartridge.

2. The cartridge of claim 1, wherein the length of the filter ranges from about 2 mm to about 30 mm.

3. The cartridge of claim 1, wherein the filter is detachable from the cartridge.

4. The cartridge of claim 1, wherein the filter includes a sleeve configured to attach the filter to the cartridge.

5. The cartridge of claim 1, further comprising:

a mouthpiece at the mouth end of the cartridge, the filter between the heater and the mouthpiece.

6. The cartridge of claim 1, wherein the filter comprises:

at least one additive.

7. The cartridge of claim 6, wherein the at least one additive includes flavor, an aerosol modifier, an aromatic material, a pH modifying agent, a chemesthesis agent, or any combination thereof.

8. The cartridge of claim 6, wherein the at least one additive is impregnated in the filter.

9. The cartridge of claim 6, wherein the filter comprises:

a coating on at least one surface of the filter, the at least one additive in the coating.

10. The cartridge of claim 6, wherein the at least one additive is encapsulated.

11. The cartridge of claim 6, wherein the at least one additive is dispersed substantially uniformly throughout the filter.

\* \* \* \* \*